United States Patent

Seiler, Jr.

[11] 4,082,667
[45] Apr. 4, 1978

[54] PROPORTIONING SYSTEM

[75] Inventor: William Seiler, Jr., Van Nuys, Calif.

[73] Assignee: David Kopf Systems, Tujunga, Calif.

[21] Appl. No.: 841,103

[22] Filed: Oct. 11, 1977

[51] Int. Cl.² .............................................. B01D 31/00
[52] U.S. Cl. .............................. 210/96 M; 210/321 B; 137/92
[58] Field of Search ............... 210/22 R, 96, 321, 136, 210/194; 137/60 H, 92, 536

[56] References Cited

U.S. PATENT DOCUMENTS

| 3,847,809 | 11/1974 | Kopf ....................................... 210/22 |
| 3,899,422 | 8/1975 | Williams ........................... 210/136 X |

Primary Examiner—Thomas G. Wyse
Assistant Examiner—Ferris H. Lander

[57] ABSTRACT

A proportioning system is provided for mixing dialysate used in an artificial kidney machine. A first conduit carries concentrate solution in a recirculating loop pattern. A second conduit carrying water intersects the first conduit. At the point of intersection, the first conduit has an orifice for discharging concentrate into the flowing water. Concentrate is supplied to the first conduit through a supply line immersed in a storage jug. The supply line has a pressure-operated check valve through which concentrate passes only when required.

1 Claim, 2 Drawing Figures

PROPORTIONING SYSTEM

This invention relates generally to artificial kidney machines and in particular to an improvement in the proportioning system shown in U.S. Pat. No. 3,847,809 dated Nov. 12, 1974, entitled "Proportioning System" which is hereby incorporated herein by reference.

U.S. Pat. No. 3,847,809 discloses a proportioning system in which concentrate is discharged through an orifice into a stream of water flowing past the orifice in which the rate of discharge of concentrate through the orifice is automatically controlled. The patent discloses a concentrate storage jug into which both ends of the concentrate conduit are immersed. All of the concentrate which is pumped past the orifice is returned to the concentrate storage jug. Conversely, a concentrate pump pumps concentrate directly out of the storage jug. This configuration requires relatively high flow rates of concentrate through the filter located at the opening of the concentrate supply conduit. The concentrate pump requires priming at start-up.

According to the present invention, the conduit carrying the concentrate is formed as a recirculating loop. The recirculation loop is connected to the concentrate storage jug by a concentrate supply line. The supply line has a pressure-actuated check valve which opens in response to vacuum generated by the concentrate pump. As a consequence, the concentrate system is self-priming and operates with a much smaller demand on the supply line connected to the storage jug. Therefore, it is possible to use higher quality inlet filters while maintaining relatively high flow rates of concentrate through the concentrate recirculation loop.

A primary object of the invention is to provide an improved proportioning system which is self-priming.

A further object of the invention is to provide an improved proportioning system for artificial kidney machines in which the concentrate is recirculated through a recirculation loop which is connected to a storage jug through a pressure-actuated check valve.

A further object of the invention is to provide an improved proportioning system for artificial kidney machines in which high-quality inlet filters may be used in conjunction with relatively high-capacity concentrate pumps.

Further objects and advantages of the invention will become apparent from the following description of the preferred embodiment and the drawings in which.

The instant invention is an improvement in the proportioning system of U.S. Pat. No. 3,847,809. The control circuits and mechanical design of the proportioning system are as disclosed in U.S. Pat. No. 3,847,809, except as noted herein. The instant invention resides in the design of the conduits supplying the concentrate.

Figure 1:
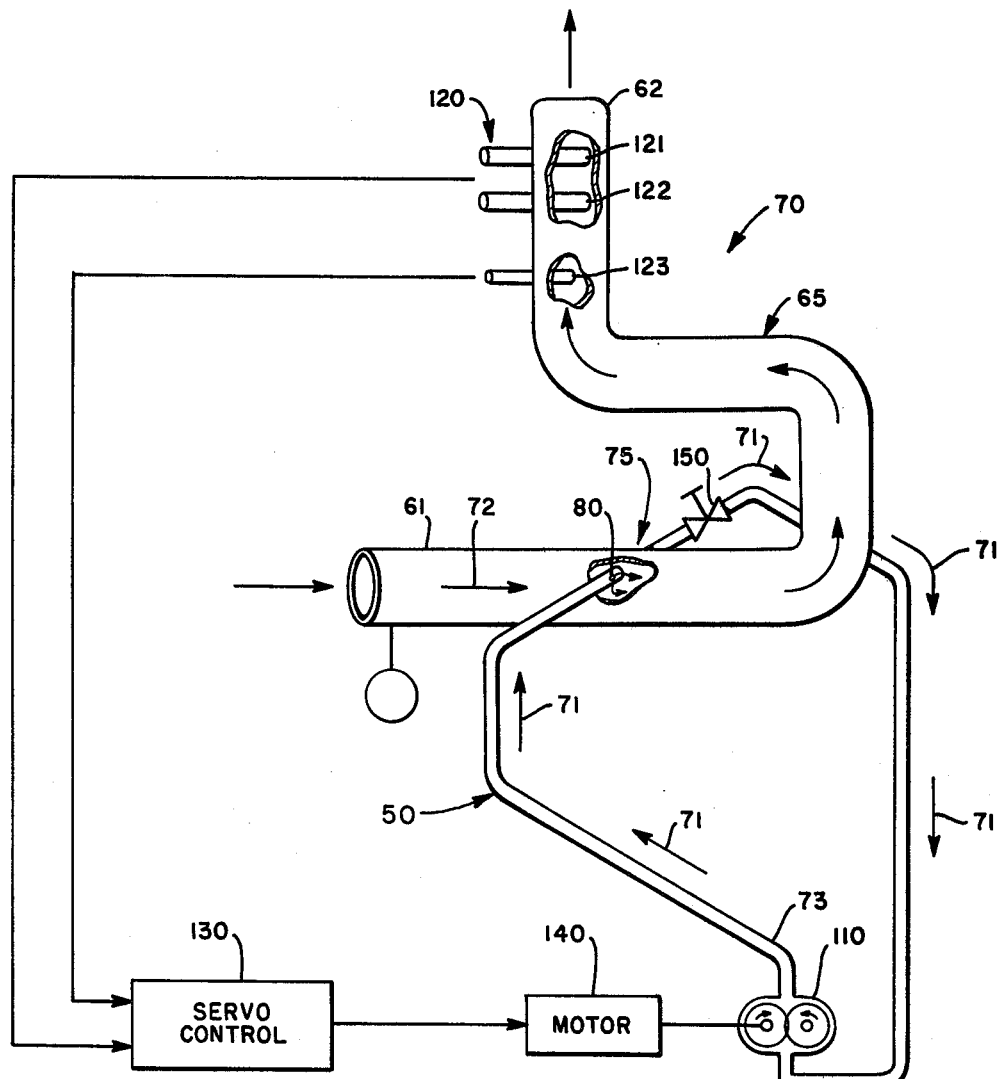
FIG. 1 is a schematic representation of the invention.
Figure 2:
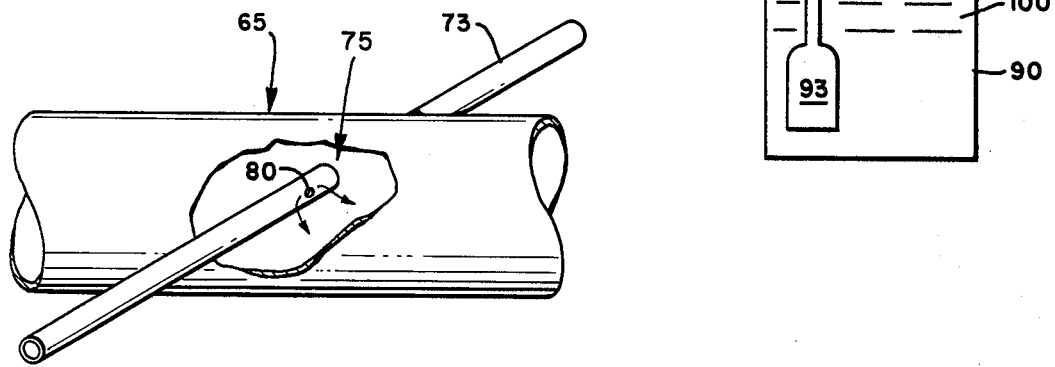
FIG. 2 is a schematic view, partially in section, of a portion of the proportioning system.

Referring to FIG. 1, the proportioning device combines concentrate solution flowing through first conduit 73 with a flow stream of water flowing at different rates through a second conduit 65. The flow path 72 of the water through the proportioning device extends from point 61 to point 62 of conduit 65. The flow path of concentrate is shown by arrows 71 and arrow 77. The flow paths 71 and 72 intersect at a point noted generally as 75 shown in greater detail in FIG. 2.

At intersection or mixing point 75, conduit 73 contains an orifice 80 which allows concentrate to escape into flow path 72 in conduit 65 and thereby mix with the water flowing along path 72.

Only a small portion of the circulating concentrate is discharged through orifice 80. The flow rate of concentrate recirculated through conduit 73 is large compared to the amount of concentrate discharged through orifice 80. The ratio of cross-sectional areas of conduit 73 and orifice 80 is about twenty to one. The diameter of conduit 73 if 0.063 in. and the diameter of orifice 80 is 0.0135 in. This ratio allows the use of a relatively large capacity concentrate pump 110 to control relatively low flow rates of concentrate through orifice 80.

Measuring means 120 includes conductivity probes 121 and 122 mounted in conduit 65 downstream of intersection 75 to monitor the proportion of concentrate in the flow stream of dialysate in conduit 65. A servo control 130, motor 140 and variable restriction 150 cooperate to control the speed of motor 110 and consequently the rate of discharge of concentrate through orifice 80. Thermistor 123 makes up one leg of a bridge circuit for servo control 130. The control mechanism is described in detail in U.S. Pat. No. 3,847,809. The control system of the present invention incorporates a variable restriction 150 in place of restriction 150 shown in U.S. Pat. No. 3,847,809.

The present invention resides in the design of a recirculation loop 50 in first conduit 73 which carries concentrate past orifice 80, through variable restriction 150 and back through concentrate pump 110. Recirculation loop 50 is connected to concentrate storage jug 90 containing concentrate solution 100 through concentrate supply line 78. Inlet filter 93 is carried by the end of supply line 78.

Check valve 76 is mounted in concentrate supply line 78 and opens when a vacuum is applied to it by concentrate pump 110.

One advantage of the concentrate circuit is that it is self-priming. During start-up of a completely dry concentrate circuit, the water in flow stream 72 exerts a pressure on orifice 80, compresses air in recirculation loop 50 and flows into conduit 73, flowing to the suction side of pump 110, wetting the gears and providing sufficient prime to permit pump 110 to exert a vacuum on check valve 76 to draw concentrate through supply line 78 along the path shown by arrow 77. Residual air in recirculation loop 50 is shortly purged through orifice 80 and discharged from the machine during normal warm-up.

The use of the check valve 76 prevents dilution of concentrate through orifice 80 during the machine rinse cycle and prevents the addition of sterilant or bleach to the concentrate during cleaning of the machine. Without check valve 76, shut-off valves must be incorporated in conduit 73 upstream and downstream of intersection 75 to prevent dilution of concentrate and to prevent addition of sterilant or bleach to the concentrate during the rinse cycle.

The instant invention allows the use of filters having increased capability. It is desirable to maximize the flow rate of concentrate past orifice 80 to increase accuracy of control and to prevent plugging of orifice 80 with particulate matter. These flow rates past orifice 80 in conduit 73 are of the order of magnitude of 750 cc/min. Using the prior system shown in U.S. Pat. No. 3,847,809, this relatively high flow rate passes through inlet filter 93, requiring either that the filter be relatively large and unwieldy or that the filter openings be relatively large. According to the present invention, the flow rate of concentrate through filter 93 is equal to the flow rate of concentrate through orifice 80. For a dialysate flow rate of 500 cc/min., the flow rate of concentrate through filter 93 is approximately 15 cc/min. and for dialysate flow rate of 250 cc/min., the flow rate of concentrate through filter 93 is approximately 7.5 cc/min. The flow rate of concentrate in recirculation loop 50 is independent of the flow rate of concentrate through filter 93. It is, therefore, possible to use smaller filters with smaller filter openings, resulting in less variation in pump suction pressure should the filter become partially occluded. These lower flow rates through concentrate supply line 78 reduce the tendency for supply line 78 to collapse. Supply line 78 is very flexible to allow easy interchanging of storage jugs 90.

I claim:

1. In a proportioning system used in an artificial kidney machine for mixing concentrate stored in a concentrate storage jug with water in predetermined proportions having a first conduit through which concentrate flows at a controlled pressure, a second conduit through which water flows, the surface of said first conduit having an orifice through which a portion of said concentrate flowing through said first conduit is discharged into said second conduit at a mixing point with the remainder of said concentrate continuing to flow in said first conduit past said orifice, and control means cooperating with said measuring means for controlling the rate at which concentrate passes through said orifice, thereby maintaining the desired mix proportions of water and concentrate, the improvement comprising:

a recirculation loop formed by said first conduit,
a concentrate supply line connecting said concentrate storage jug with said recirculation loop, and
a check valve in said concentrate supply line which opens at a predetermined pressure in said recirculation loop, whereby concentrate flows from said concentrate storage jug to said recirculation loop when said check valve opens.

* * * * *